United States Patent [19]

Grew et al.

[11] 4,438,046

[45] Mar. 20, 1984

[54] QUATERNARY AMMONIUM SALTS

[75] Inventors: Edward L. Grew, Huntingdon, England; Nigel D. V. Wilson, Midlothian, Scotland

[73] Assignee: Glaxo Group Limited, London, England

[21] Appl. No.: 372,850

[22] Filed: Apr. 29, 1982

[30] Foreign Application Priority Data

Apr. 30, 1981 [GB] United Kingdom ............... 8113416
Aug. 14, 1981 [GB] United Kingdom ............... 8124864

[51] Int. Cl.$^3$ .......................... C07C 87/68; C12F 5/00
[52] U.S. Cl. ............................. 260/501.15; 564/164; 252/365; 252/366
[58] Field of Search ................ 260/501.15; 564/164; 260/501.15; 252/365, 366

[56] References Cited

U.S. PATENT DOCUMENTS 3,080,326  3/1963  Samuel ........................... 564/164
3,080,327  3/1963  Hay ................................. 564/164

FOREIGN PATENT DOCUMENTS 955309  4/1964  United Kingdom ............... 564/164

OTHER PUBLICATIONS

Glover et al., Chem. Abst., vol. 78, #75768, (1973).

*Primary Examiner*—James H. Reamer
*Attorney, Agent, or Firm*—Bacon & Thomas

[57] ABSTRACT

The invention provides novel lignocaine benzyl benzoate hydrate which may be prepared by agitating a solution of lignocaine benzyl benzoate in water at a concentration of at least 5% w/w and at a temperature of 10° to 35° C. Anhydrous lignocaine benzyl benzoate may be prepared by heating the hydrate. The resulting anhydrous benzyl benzoate or the hydrate itself may be used, for example in the form of an aqueous solution, to denature organic substances such as ethyl alcohol.

9 Claims, No Drawings

QUATERNARY AMMONIUM SALTS

This invention relates to a quaternary ammonium salt and to a process for its preparation. In particular, the invention is concerned with a process for the preparation of lignocaine benzyl benzoate.

Lignocaine is the approved name for N,N-diethylamino-2,6-dimethylacetanilide.

Lignocaine benzyl benzoate [benzyldiethyl(2:6-xylyl-carbamoylmethyl ammonium benzoate], also known as denatonium benzoate, has the formula:

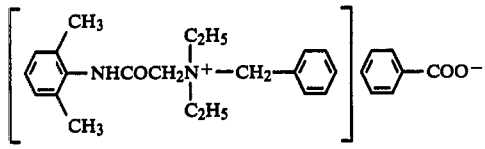

and is described and claimed in British patent specification No. 955,309. It is the most bitter substance known to man and is thus used where an intensely bitter taste is required for medicinal or industrial purposes. It may be added to toxic substances as a deterrent to accidental ingestion and may be used as a denaturant for alcohol.

In the final stage of preparation, the above British Specification describes in Example 1 the addition of an alkanoic solution of benzoic acid to an alkanoic solution of lignocaine benzyl hydroxide. After concentration and trituration with di-ethyl ether, the product, lignocaine benzyl benzoate, is recrystallised from mixtures of ethyl acetate and isopropanol or chloroform, or from a mixture of ethanol and diisopropyl ether or from methyl ethyl ketone. An alternative preparation is described in Example 3 wherein an aqueous solution of lignocaine benzyl hydroxide is neutralised with benzoic acid, the solution is evaporated to dryness and the resulting lignocaine benzyl benzoate is recrystallised from a mixture of ethanol and diisopropyl ether.

We have now found that lignocaine benzyl benzoate may be crystallised directly and in a high yield from solutions in water to give, initially, a lignocaine benzyl benzoate hydrate. Crystallisation of lignocaine benzyl benzoate directly from water is particularly advantageous in that it avoids the need for hazardous, inflammable organic solvents such as the ethers previously employed in the crystallisation procedure which necessitated, the use of flame-proof equipment in a specially designed flame proof area. This aqueous crystallisation process also permits direct recovery of the compound from aqueous reaction mixtures.

Thus, according to our invention, we provide a process for the crystallisation of lignocaine benzyl benzoate which comprises agitating a solution of lignocaine benzyl benzoate in water at a concentration of at least 5% w/w and at a temperature of 10° to 35° C., followed by the recovery of the crystals of lignocaine benzyl benzoate hydrate thus formed.

The crystalline product is novel and thus, according to another aspect of the invention, we provide lignocaine benzyl benzoate hydrate. We have found the water content of the lignocaine benzyl benzoate hydrate to be in the range of 3.6 to 4.1% w/w.

According to a particular embodiment of this invention there is provided crystalline lignocaine benzyl benzoate hydrate having the characteristic x-ray data substantially as herein described in Example 10 and the characteristic infra-red data as herein described in Examples 1 and 10. The water content together with the x-ray and infra-red data suggest that the product is in the form of a "wet" hemihydrate.

In the process according to this invention concentrations of lignocaine benzyl benzoate in water of, for example, 10 to 50% w/w may be used in the crystallisation process, preferably 15 to 30% w/w and particularly about 20 to 25% w/w. These concentrations may be achieved by preparing solutions in water at an elevated temperature, for example at from 35° to 50° C., followed by cooling to the desired temperature for initiation of the crystallisation process. It is preferred to maintain temperatures of from 20° to 25° C. throughout the crystallisation process.

The presence of a seed of lignocaine benzyl benzoate hydrate is preferred to induce crystallisation and it is convenient to continue agitating for from 24 to 48 hours in order to achieve an optimum yield of crystals. The crystals may be readily recovered by conventional methods (e.g. filtration or centrifugation) and may be washed, for example, with a small amount of water. The resulting crystals of the hydrate may then be dried at temperatures of from 15° to 30° C., for example by forced ventilation.

The liquor remaining following removal of the crystals of the hydrate may be concentrated and reprocessed according to the above method to provide further crops of crystals.

According to a still further aspect of the invention we provide a process for the conversion of lignocaine benzyl benzoate hydrate to anhydrous lignocaine benzyl benzoate by heating the hydrate.

The hydrate may be heated, for example, at a temperature of from 75° to 110° C., preferably from 90° to 110° C. in order to obtain the anhydrous lignocaine benzyl benzoate.

Inorganic or organic substances, preferably ethyl alcohol can be denatured, i.e. rendered unpotable or inedible, by dissolving in or mixing with them a minor proportion of lignocaine benzyl benzoate. According to the present invention the lignocaine benzyl benzoate may be used for the purpose of denaturing substances, especially ethyl alcohol, in the form of the lignocaine benzyl benzoate hydrate or in the form of anhydrous lignocaine benzyl benzoate prepared by heating the hydrate.

The lignocaine benzyl benzoate, in the anhydrous or hydrated form, may be incorporated in the organic or inorganic substances in minor proportions as described in British patent specification No. 955,309. For example, concentrations of less than 0.01% by weight of the lignocaine benzyl benzoate are generally sufficient to denature the substance in which it is incorporated. The bitterness is apparent at concentrations as low as 0.0005% by weight. In the case of ethyl alcohol, a concentration of about 0.005% by weight of the lignocaine benzyl benzoate may generally be employed; the preferred concentration being from 0.01% to 0.001% by weight.

According to the invention, the lignocaine benzyl benzoate hydrate, or the anhydrous lignocaine benzyl benzoate prepared therefrom, may conveniently be used in the form of an aqueous solution having a concentration of, for example, 0.1 to 5% by weight.

The following Examples illustrate the invention. All temperatures are in °C.

EXAMPLE 1

Lignocaine benzyl benzoate (20 g) was dissolved in deionised water (80 g) with stirring and warming to 40°. The resulting solution (20% w/w) was cooled to 20° in a cold water bath and stirred magnetically for 24 hours. The product was obtained as a fine white, crystalline solid which was filtered off and washed with deionised water (20 ml). The damp cake was dried in a dish by forced ventilation at 20° until weight loss was minimal, to yield crystals of lignocaine benzyl benzoate hydrate (15.74 g); $\gamma$max (KBr discs) 1688 (>C=O), 1535, 1475, 1270, 865 and 808 cm$^{-1}$.

EXAMPLE 2

A sample of the lignocaine benzyl benzoate hydrate obtained in Example 1 (1.04 g) was further dried at 105° to constant weight to yield anhydrous lignocaine benzyl benzoate (0.99 g) identical to an authentic sample; $\nu$max (KBr discs) 1680 (>C=O), 1400, 880, 735 and 610 cm$^{-1}$.

EXAMPLE 3

Lignocaine benzyl benzoate (20 g) was dissolved in water (100 g) at 40° and was cooled to room temperature. A seed of lignocaine benzyl benzoate hydrate was added and the solution (17% w/w) was stirred at between 15° and 25° for 27 hours. The product was recovered and dried by the methods of Example 1 to yield lignocaine benzyl benzoate hydrate (15.8 g).

The filtrate was concentrated and crystallised in a similar manner to yield a further crop of lignocaine benzyl benzoate hydrate (2.8 g).

EXAMPLE 4

A 10% w/w solution of lignocaine benzyl benzoate in deionised water (200 g total weight) was prepared with stirring and warming to 35°. The solution was filtered through a porosity 3 sintered glass filter funnel to remove insoluble matter and was cooled to 20° before seeding with lignocaine benzyl benzoate hydrate. Stirring was maintained at 20° for 24 hours and the lignocaine benzyl benzoate solid was then filtered off, drained, and dried to constant weight by forced ventilation at 15°–20° to give lignocaine benzyl benzoate hydrate.

EXAMPLE 5

Lignocaine benzyl benzoate (30.0 g) was dissolved in deionised water (70.0 g) with stirring and warming to 35°. The resulting 30% w/w solution was cooled, seeded with lignocaine benzyl benzoate hydrate and stirred at 20° for 24 hours. The resulting solid was filtered off and dried by forced ventilation at ambient temperature to give lignocaine benzyl benzoate hydrate (25.97 g).

EXAMPLE 6

A 20% w/w aqueous solution was prepared from lignocaine benzyl benzoate (20.0 g) and deionised water (80.0 g) with stirring and warming to 35°. After filtration through a porosity 3 sintered glass filter funnel the solution was stirred at 35°–37° for 24 hours. The solution was seeded with lignocaine benzyl benzoate hydrate and stirred for a further 24 hours at 35°. The small amount of white crystalline solid which had separated was filtered off, drained and dried at ambient temperature to constant weight to give lignocaine benzyl benzoate hydrate.

EXAMPLE 7

The product of Example 4 was further dried at 106° for two hours to yield anhydrous lignocaine benzyl benzoate (11.05 g).

EXAMPLE 8

The lignocaine benzyl benzoate hydrate obtained in Example 5 was further dried at 106° for 3½ hours to give anhydrous lignocaine benzyl benzoate (24.94 g).

EXAMPLE 9

The product of Example 6 was further dried at 106° to constant weight to yield anhydrous lignocaine benzyl benzoate (0.55 g).

EXAMPLE 10

Lignocaine benzyl benzoate (100 g) was dissolved in deionised water (300 g) with stirring and warming to 40°. The resulting solution (25% w/w) was filtered through a scintered glass funnel and seeded with lignocaine benzyl benzoate hydrate. The solution was cooled to 20° C. in a cold water bath and stirred magnetically for 24 hours. The product was obtained as a fine white, crystalline solid which was filtered off and washed with deionised water (100 ml). The damp cake was dried in a dish by forced ventilation at ambient temperature until weight loss was minimal, to yield crystals of lignocaine benzyl benzoate hydrate (83.3 g); $\nu$max (Nujol Mull) 3436 s, 2770 s, 1694 s, 1648 w, 1608 s, 1596 s, 1574 s, 1568 sh, 1538 s, 1498 w, 1408 w, 1312 m, 1288 m, 1272 m, 1252 m, 1160 w, 1030 w, 782 s, 758 m, 724 s, 704 s and 676 s cm$^{-1}$.

The X-ray diffraction pattern of lignocaine benzyl benzoate hydrate may be obtained by loading the material into a 0.3 mm diameter glass capillary and photographing the patterns by the Debye Scherrer method in a 114.6 mm diameter camera by exposure for 12 hours to CoK$_\alpha$ radiation and for 3 hours to CuK$_\alpha$ radiation. The weighted mean values of X-ray wavelengths used for the calculations were CuK$_\alpha$=1.54171 Å and CoK$_\alpha$=1.79024 Å.

The X-ray diffraction pattern of a sample of lignocaine benzyl benzoate hydrate prepared by the method just described in terms of 'd' spacings and intensities of the lines is given in the following Table.

TABLE

| d(Å) | Intensity | d(Å) | Intensity |
|------|-----------|------|-----------|
| 13.92 | m | 3.30 | w |
| 10.83 | m | 3.19 | vw |
| 9.71 | s | 3.11 | m |
| 7.70 | m | 2.93 | wd |
| 7.02 | s | 2.79 | wd |
| 5.82 | m | 2.72 | w |
| 5.45 | s | 2.58 | vw |
| 5.21 | m | 2.47 | vw |
| 4.82 | ms | 2.41 | vw |
| 4.71 | w | 2.37 | vw |
| 4.33 | m | 2.30 | w |
| 4.21 | w | 2.12 | vw |
| 3.90 | vs | 2.04 | w |
| 3.73 | w | 1.99 | vw |
| 3.63 | m | 1.94 | vw |
| 3.54 | m | 1.86 | vw |
| 3.37 | m | 1.84 | w | s = strong; m = medium; w = weak v = very; d = diffuse

We claim:

1. Crystalline lignocaine benzyl benzoate hydrate.

2. Crystalline lignocaine benzyl benzoate hydrate according to claim 1, having the characteristic infra-red data substantially as as follows: $\nu$max (KBr discs) 1688 (>C=O), 1535, 1475, 1270, 865 and 808 cm$^{-1}$.

3. A method of denaturing an inorganic or organic substance which comprises mixing therewith or dissolving therein a minor proportion of lignocaine benzyl benzoate hydrate.

4. A method of denaturing an inorganic or organic substance according to claim 3, wherein the minor proportion is from about 0.01% to 0.001% by weight.

5. A method according to claim 3, wherein the organic substance is ethyl alcohol.

6. An inorganic or organic substance which has been denatured by the incorporation therein of a minor proportion of lignocaine benzyl benzoate hydrate.

7. Ethyl alcohol which has been denatured by the incorporation therein of a minor proportion of lignocaine benzyl benzoate hydrate.

8. Crystalline lignocaine benzyl benzoate hydrate according to claim 1 wherein the water content is in the range of 3.6 to 4.1% w/w.

9. Crystalline lignocaine benzyl benzoate hydrate according to claim 2, having the characteristic infrared and x-ray diffraction data substantially as respectively follows: $\nu$max (Nujol Mull) 3436 s, 2770 s, 1694 s, 1648 w, 1608 s, 1596 s, 1574 s, 1568 sh, 1538 s, 1498 w, 1408 w, 1312 m, 1288 m, 1272 m, 1252 m, 1160 w, 1030 w, 782 s, 758 m, 724 s, 704 s and 676 s cm$^{-1}$; an x-ray diffraction pattern as in the following table:

TABLE

| d(Å) | Intensity | d(Å) | Intensity |
|------|-----------|------|-----------|
| 13.92 | m | 3.30 | w |
| 10.83 | m | 3.19 | vw |
| 9.71 | s | 3.11 | m |
| 7.70 | m | 2.93 | wd |
| 7.02 | s | 2.79 | wd |
| 5.82 | m | 2.72 | w |
| 5.45 | s | 2.58 | vw |
| 5.21 | m | 2.47 | vw |
| 4.82 | ms | 2.41 | vw |
| 4.71 | w | 2.37 | vw |
| 4.33 | m | 2.30 | w |
| 4.21 | w | 2.12 | vw |
| 3.90 | vs | 2.04 | w |
| 3.73 | w | 1.99 | vw |
| 3.63 | m | 1.94 | vw |
| 3.54 | m | 1.86 | vw |
| 3.37 | m | 1.84 | w | s = strong; m = medium; w = weak v = very; d = diffuse

* * * * *